United States Patent [19]

Hata et al.

[11] Patent Number: 4,871,539

[45] Date of Patent: Oct. 3, 1989

[54] BIODEODORIZER AND PROCESS FOR PREPARING SAME

[75] Inventors: Kosei Hata; Toshiyuki Maruoka, both of Osaka, Japan

[73] Assignee: Seikenkai Foundational Juridical Person, Osaka, Japan

[21] Appl. No.: 755,985

[22] Filed: Jul. 17, 1985

[51] Int. Cl.$^4$ .......................... A61K 35/74; C12N 1/20
[52] U.S. Cl. .................... 424/93; 435/252.9; 435/253.4; 435/853; 435/885; 435/832
[58] Field of Search ................. 424/93; 435/853, 885, 435/832, 253, 252.9, 253.4

[56] References Cited

U.S. PATENT DOCUMENTS

| | | | |
|---|---|---|---|
| 3,494,832 | 2/1970 | Florent et al. | 195/48 |
| 3,852,158 | 12/1974 | Anderson et al. | 195/100 |
| 3,957,974 | 5/1987 | Hata | 424/93 |
| 4,314,995 | 2/1982 | Hata et al. | 424/93 |
| 4,345,032 | 8/1982 | Hata | 435/253 |
| 4,425,366 | 1/1984 | Sozzi et al. | 426/43 |

FOREIGN PATENT DOCUMENTS

| | | |
|---|---|---|
| 0099235 | 1/1984 | European Pat. Off. . |
| 0930107 | 7/1963 | United Kingdom . |
| 1584693 | 2/1981 | United Kingdom . |
| 1584694 | 2/1981 | United Kingdom . |

OTHER PUBLICATIONS

Chem. Abs., vol. 9, 1979, p. 239, Abs. No. 90:68903k, Smither (1978), J. Appl. Bacteriol 45(2), 267-77.

*Primary Examiner*—Thomas G. Wiseman
*Assistant Examiner*—Charles L. Patterson, Jr.
*Attorney, Agent, or Firm*—Sughrue, Mion, Zinn, Macpeak & Seas

[57] ABSTRACT

A biodeodorizer and a process to prepare the biodeodorizer which comprises (a) at least one strain selected from the group consisting of *Lactobacillus deodorans*, *Lactobacillus clearans* and a mixed strain of *Lactobacillus sulfurica* and *Lactobacillus nitrosus*, and (b) *Streptococcus faecalis* having the ability to produce antibiotics.

1 Claim, No Drawings

BIODEODORIZER AND PROCESS FOR PREPARING SAME

FIELD OF THE INVENTION

The present invention relates to a biodeodorizer and a process for preparing the same and, more particularly, to a biodeodorizer comprising a mixture of certain Lactobacillus strains and *Streptococcus faecalis*.

BACKGROUND OF THE INVENTION

It is already known to use various microorganisms for deodorizing decomposing matter and the like, or for reducing or removing offensive odors arising from decomposing matter or the like. Some bacteria have been used in vivo and some bacteria have been used in the environment by dispersion. For instance, Japanese Patent Publication No. 7297/83 and British Pat. No. 1,584,693 teach that bacteria which are used in the environment by dispersion have a deodorizing function. Further, microorganisms having a deodorizing function in vivo were already developed by the inventors concerned. (For instance, see U.S. Pat. No. 4,345,032, British Pat. No. 1,584,694, etc.)

Among these deodorant microorganisms for use in vivo *Lactobacillus deodorans*, *Lactobacillus clearans*, *Lactobacillus sulfurica*, *Lactobacillus nitrosus*, etc. are mentioned as preferred.

These deodorant microorganisms, however, have the disadvantage that, when they were administered to man and animals, the deodorant effects attained were not always the same but varied depending on the individual or on the animal species and on the conditions of administration, even when the same strains were administered in the same amount. Therefore, it has been desired to make further improvements so that a definite or fixed effect could be attained by administration of these microorganisms to man and animals, irrespective of the individual or animal species.

Under these circumstances, various investigations have now been made to heighten the deodorant effect of *Lactobacillus deodorans*, *Lactobacillus clearans*, *Lactobacillus sulfurica* and *Lactobacillus nitrosus* and overcome the defects as described above, and the present invention has been accomplished.

SUMMARY OF THE INVENTION

Thus, an object of the present invention is to provide a novel biodeodorizer and a process for preparing the same.

Another object of the present invention is to provide a novel biodeodorizer exhibiting, on application to man and animals, a fixed deodorant effect irrespective of the individual and animal species and the conditions of administration, and a process for preparing the same.

A further object of the present invention is to provide a biodeodorizer exhibiting, on administration to man and animals, an excellent and durable deodorant effect irrespective of the individual and animal species and the conditions of administration, and a process for preparing the same.

Another object of the present invention is to provide a biodeodorizer exhibiting, on administration to man and animals, a deodorant effect which occurs within a short time after administration and lasts for a long time after stopping administration, irrespective of the individual and animal species and the conditions of the administration, and a process for preparing the same.

It has now been found after earnest investigations that the above objects are attained by using the above-mentioned microorganisms in combination with an other certain microorganism, rather than by improving the microorganisms per se.

The objects as described above of the present invention have been attained by using (a) at least one Lactobacillus strain selected from the group consisting of *Lactobacillus deodorans*, *Lactobacillus clearans* and a mixed culture of *Lactobacillus sulfurica* and *Lactobacillus nitrosus*, all belonging to deodorant Lactobacillus, in combination with (b) *Streptococcus faecalis* having the ability to produce antibiotics.

Thus, the present invention provides a biodeodorizer comprising (a) at least one strain selected from the group consisting of *Lactobacillus deodorans*, *Lactobacillus clearans* and a mixed strain of *Lactobacillus sulfurica* and *Lactobacillus nitrosus*, and (b) *Streptococcus faecalis* having the ability to produce antibiotics.

The present invention provides a process to prepare a biodeodorizer comprising mixing (a) at least one strain selected from the group consisting of *Lactobacillus deodorans*, *Lactobacillus clearans* and a mixed strain of *Lactobacillus sulfurica* and *Lactobacillus nitrosus*, and (b) *Streptococcus faecalis* having the ability to produce antibiotics.

The present invention further provides a biodeodorizer comprising a combination of (a) at least one strain selected from the group consisting of *Lactobacillus deodorans*, *Lactobacillus clearans* and a mixed strain of *Lactobacillus sulfurica* and *Lactobacillus nitrosus*, (b) *Streptococcus faecalis* having the ability to produce an antibiotic, and further (c) a Bifidobacterium strain and/or a Bacillus strain.

The present invention provides a process to prepare a biodeodorizer comprising mixing (a) at least one strain selected from the group consisting of *Lactobacillus deodorans*, *Lactobacillus clearans*, and a mixed strain of *Lactobacillus sulfurica* and *Lactobacillus nitrosus*, (b) *Streptococcus faecalis* having the ability to produce antibiotics and (c) a Bifidobacterium strain and/or a Bacillus strain.

DETAILED DESCRIPTION OF THE INVENTION

The characteristics of the *Lactobacillus deodorans* used in the present invention, and a method of isolating it, are described in Japanese Patent Publication No. 49193/82, corresponding to U.S. Pat. No. 4,345,032, *Lactobacillus deodorans* has the following properties:

(1) (a) Odoriferous compounds containing sulfur atoms (such as $Na_2S \cdot 9H_2O$) and odoriferous compounds containing nitrogen atoms (such as $NH_3$) are essential substances for growth of *Lactobacillus deodorans*. For example, even when *Lactobacillus deodorans* cannot grow in Stephanson-Whetham(S-W) medium only, it becomes capable of growing in the presence of such odoriferous compounds containing sulfur atoms and/or such odoriferous compounds containing nitrogen atoms.

(b) When *Lactobacillus deodorans* is cultured in a medium used for the culture according to the present invention, for example, Stephenson-Whetham medium to which Casamino acids and vitamins are added, growth is promoted or accelerated by adding odoriferous compounds containing sulfur atoms, odoriferous compounds containing nitrogen atoms and/or odoriferous compounds containing carbon atoms to the medium during the logarithmic growth stage.

(c) When such odoriferous compounds containing a sulfur atom, odoriferous compounds containing a nitrogen atom and/or odoriferous compounds containing a carbon atom are present in the culture medium, *Lactobacillus deodorans* continues to grow until these compounds are consumed or assimilated completely.

(2) *Lactobacillus deodorans* has low auxotrophy and can grow in Stephanson-Whetham medium consisting of inorganic salts and sugar or in such Stephanson-Whetham medium to which either Casamino acids or vitamins are added.

(3) *Lactobacillus deodorans* has a high assimilating power for decomposing matters and an strong intestinal stationary ability. Namely, ability to survive in the intestine on a stationary basis, i.e., it has strong intestinal stationary ability. Namely, *Lactobacillus deodorans* has an ability to exclude or clean noxious substances or to take the noxious substances into its body, i.e., it has a strong cleaning power in vivo.

(4) *Lactobacillus deodorans* is a non-pathogenic strain.

(5) To maintain the strong deodorant power of *Lactobacillus deodorans*, it is desirable to incorporate amino acids containing sulfur atoms and/or odoriferous compounds containing sulfur atoms, nitrogen atoms or carbon atoms the the nutrient medium.

(6) For the storage of the cell body, it is desirable to place those substances as mentioned above and/or glycine, glutamic acid, lysine, alanine, phenylalanine, alginine, aspartic acid, etc. around the cell body of *Lactobacillus deodorans*.

Any strains of *Lactobacillus deodorans* which are prepared according to an isolation method of the above Publication or which have the above described characteristics may be used in the present invention.

Especially preferred strains of *Lactobacillus deodorans* which can be used in the present invention are those strains deposited at the Agency of Industrial Science & Technology, Fermentation Research Institute (Japan) under Domestic Registration FERM-P Nos. 1946, 2742, 2779, 2780, 2781 and 2782. FERM-P Nos. 1946 and 2779 are deposited also at the Institute of Fermentation, Osaka, Japan under International Registration IFO Nos. 14450 and 14451.

The characteristics of *Lactobacillus clearans* used in the present invention, and a method of isolating it, are described in Japanese patent application (OPI) No. 11,177/84, corresponding to U.S. Pat. No. 4,579,734, and in U.S. Pat. No. 4,579,734. (The term "OPI" as used herein refers to a "published unexamined Japanese Patent Application".) *Lactobacillus clearans* has the following characteristics.

(1) (a) Odoriferous compounds containing sulfur atoms such as $Na_2S.9H_2O$), odoriferous compounds containing nitrogen atoms (such as $NH_3$) and/or odoriferous compounds containing carbon atoms (such as a lower fatty acids) are not essential for the growth of *Lactobacillus clearans*. A medium in which *Lactobacillus clearans* does not grow cannot be changed to one in which *Lactobacillus clearans* can grow, even by addition of the above-mentioned substances.

(b) Promotion or acceleration of growth does not occur by adding odoriferous compounds containing sulfur atoms, odoriferous compounds containing nitrogen atoms and/or odoriferous compounds containing carbon atoms to the culture medium for *Lactobacillus clearans* at the logarithmic growth stage.

(c) *Lactobacillus clearans* utilizes or assimilates both odoriferous compounds containing sulfur atoms and odoriferous compounds containing nitrogen atoms to some degree. (Many strains utilize about 30 to about 90% thereof.) However, *Lactobacillus clearans* cannot utilize these materials completely. That is to say, they remain unutilized. (It is noted that *Lactobacillus deodorans* assimilates the compounds completely.

(2) The auxotrophy of *Lactobacillus clearans* is low. It can grow in Stephanson-Whetham medium by merely adding thereto both Casamino acids and vitamins.

(3) The multiplying power of *Lactobacillus clearans* is within the range of 0.9 to about 1.1 times in meat extract bouillon, as compared with *Escherichia coli*. *Lactobacillus clearans* utilizes decomposing matter, although not completely, and so it has a cleaning power in vivo to some degree for about 2 weeks at a maximum, generally for 3 to 6 days, after administration.

(4) *Lactobacillus clearans* corresponds to the Genus Lactobacillus in all properties. However, it is quite different from previously known strains with respect to the ability of utilizing or assimilating odoriferous compounds containing sulfur atoms (such as $Na_2S.9H_2O$) and odoriferous compounds containing nitrogen atoms (such as $NH_3$), as described above. (Previously known strains except for *Lactobacillus deodorans* do not utilize these types of compounds.) Its auxotrophy is low.

(5) The intestinal stationary ability of *Lactobacillus clearans* is lower than that of *Lactobacillus deodorans*, although it is stronger than that of previously known Lactobacillus strains.)

(6) *Lactobacillus clearans* used in the present invention is a non-pathogenic strain.

(7) To maintain the strong deodorant power of *Lactobacillus clearans* used in the present invention, it is desirable to incorporate amino acids containing sulfur atoms and/or odoriferous compounds containing sulfur atoms, nitrogen atoms and/or carbon atoms in the nutrient medium.

(8) For the storage of cell body, it is desirable to place those substances as mentioned above for *Lactobacillus deodorans* around the cell body of *Lactobacillus clearans*.

Any strains of *Lactobacillus clearans* which are prepared according to the above isolation method or which have the above described characteristics may be used in the present invention.

Especially preferred strains of *Lactobacillus clearans* which can be used in the present invention are those deposited at the Agency of Industrial Science & Technology, Fermentation Research Institute (Japan) under Domestic Registration FERM-P Nos. 6587, 6588, 6589, and 6590. Among these strains, strains of FERM-P Nos. 6587 and 6590 are deposited also at the Institute of Fermentation, Osaka, Japan under International Registration IFO Nos. 14253 and 14254.

The characteristics of *Lactobacillus sulfurica* and *Lactobacillus nitrosus* used in the present invention, and a method of isolating each of them, are described in U.S. patent application Ser. No. 511,805; now U.S. Pat. No. 4,579,734.

*Lactobacillus sulfurica* used in the present invention utilizes only odoriferous compounds containing sulfur atoms and *Lactobacillus nitrosus* utilizes only odoriferous compounds containing nitrogen atoms, although the utilization is not complete but remains at about 90% or less in each case. However, except for this property, they have the same properties as *Lactobacillus clearans*. Therefore, on carrying out deodorization in vivo with *Lactobacillus sulfurica* and *Lactobacillus nitrosus*, a satisfactory effect cannot be expected unless the two are used in combination.

Any strains of *Lactobacillus sulfurica* and *Lactobacillus nitrosus* which are prepared according to the isolating method as described above or which have the above characteristics may be used in the present invention.

Especially preferred strains of *Lactobacillus sulfurica* are those deposited at the Agency of Industrial Science & Technology, Fermentation Research Institute (Japan) under Domestic Registration FERM-P Nos. 7383 and 7384, which are also deposited at the Institute of Fermentation, Osaka, Japan under International Registration IFO Nos. 14255 and 14256, respectively, and especially preferred strains of *Lactobacillus nitrosus* are those deposited at Fermentation Research Institute the Agency of Industrial Science and Technology (Japan) under Domestic Registration FERM-P Nos. 7385 and 7386, which are also deposited at the Institute of Fermentation, Osaka, Japan under International Registration IFO Nos. 14257 and 14258, respectively.

The differences in the four types of Lactobacillus mentioned above from previously known Lactobacillus are as follows.

(1) Previously known Lactobacillus strains do not require odoriferous compounds containing sulfur atoms and odoriferous compounds containing nitrogen atoms as essential substances for their growth. Even when these odoriferous compounds are added to a culture medium in which known Lactobacillus strains cannot grow, the strains do not begin to grow. Further, even when these compounds are added at the logarithmic growth stage of the known strains, promotion or acceleration of growth does not occur. Previously known Lactobacillus strains do not at all consume these compounds, and so the compounds remain ultimately in the amount originally added. (2) The previously known Lactobacillus strains are separated according to their auxotrophy into a group of strains which can grow in Stephanson-Whetham medium by adding Casamino acids and vitamins thereto and a group of strains which cannot grow in Stephanson-Whetham medium unless other ingredients are further added thereto in addition to Casamino acids and vitamins. (3) The previously known Lactobacillus strains are inferior in multiplying power in usual medium to *Escherichia coli*, etc. (for example, 0.5 times that of *Escherichia coli*). Their intestinal stationary ability is at a degree of 1 or 2 days. The cleaning power against even odoriferous compounds containing carbon atoms is unknown.

The four kinds of Lactobacillus strains all have the following properties of Lactobacillus: That is, they are Gram-positive, anaerobic or microaerophilic, non-spore forming rods and, depending on the strains, may be spherical rod-like, curved rod-like, coryne-like or thread-like. They are non-motile, negative to catalase and do no reduce nitrates. They do not decompose gelatin and do not produce indole or hydrogen sulfide. Some of them are bipolar-stained. Their ability to decompose protein and fat is very weak, if any. They show better growth under anaerobic or microaerobic, conditions rather than under aerobic conditions, having strong ability to decompose sugars, and are acid-fast. When used for glucose fermentation, they produce lactic acid in an yield of more than 50%. Their growth is promoted by adding acetic acid. They are not pathogenic to animals and plants.

*Lactobacillus clearans* acts very mildly even when it is orally administered in a large amount and reduces offensively odoriferous substances in feces, without an uncomfortable feeling, while the administration continues. However, when administration is stopped, the strain is excreted through the intestinal tract to lose its deodorant effect in vivo within a short time.

*Lactobacillus deodorans* has a deodorant power of about several tens of times or more, compared with *Lactobacillus clearans*, and moreover it deodorizes completely, that is, it degrades offensively odoriferous substances completely. For example, human feces were deodorized completely within 48 hours by administration of a tenth part (by weight) of a culture solution of *Lactobacillus deodorans*.

The *Lactobacillus deodorans* used in the present invention is obtained by cultivation of *Lactobacillus lactis* which multiplees and is capable or not capable of producing antibiotics in either one of the minimal nutrient mediums shown in the following table, in a medium not affecting the properties of these strains, and the subsequent isolation.

| Classification | Minimal Nutrient Medium |
|---|---|
| (a) | Glucose or starch, inorganic salts and water; |
| (b) | An odoriferous compound containing sulfur; nitrogen or carbon, which is present in feces, is added to (a); |
| (c) | Vitamins are added individually or in combination, to (a); |
| (d) | Amino acids are added individually or in combination, to (a); |
| (e) | Specific vitamins are added individually or in combination, to (a); |
| (f) | Tryptophane is added to (a); |
| (g) | Amino acids containing sulfur are added individually or in combination, to (a); |

It is preferable to endow resistance against antibacterial agents, if necessary. The *Lactobacillus lactis* so obtained can be processed into preparations according to conventional methods. The above-mentioned medium not affecting the properties of *Lactobacillus lactis* is each of the minimal nutruent mediums as stated in the present invention, a combination of them, or an agar medium similar thereto. As the case may be, usual agar medium may be used intermediately.

Further, *Lactobacillus clearans* is isolated using the medium which is higher in nutrients than that for *Lactobacillus deodorans*. For example, the medium for isolation of *Lactobacillus clearans* comprises meat extract, peptone, $Na_2S.9H_2O$, sodium butyrate, glucose and agar. As a preferable medium for *Lactobacillus nitrosus*, it comprises meat extract, peptone, $NH_3$, sodium butyrate, glucose and agar. As a preferable medium for *Lactobacillus sulfurica*, it comprises meat extract, peptone, $Na_2S.9H_2O$, sodium butyrate, glucose, $CaCO_3$, and agar.

Of colonies thus appearing, colonies with margins that are transparent are screened and subjected to gas generation testing and non-gas generation cells are retained. Subsequently, cells thus obtained were subjected to hemolysis testing to obtain non-hemolytic cells and then cultured in the LBS medium. After confirmation that the cells belong to Lactobacillus, the degree of decrease of $Na_2S.9 H_2O$ and $NH_3$, and the accelerated growth for the Lactobacillus strains are examined and classified to *Lactobacillus deodorans, Lactobacillus clearans, Lactobacillus sulfurica* and *Lactobacillus nitrosus*. As to each Lactobacillus, ones which have higher values are collected. The "μ value" represents the growth rate of microorganisms growing in the logarithmic phase.

The *Lactobacillus lactis* used in the present invention was isolated, for example, in the following manner:

In a medium (A) [Stephanson Wetham medium S-W]+vitamin+agar (wherein [S-W] consists of $KH_2PO_4$ 1 g, $MgSO_4.7H_2O$ 0.7 g, NaCl 1 g, $(NH_4)_2HPO_4$ 4 g, $FeSO_4.7H_2O$ 0.03 g and glucose 5 g) or (B) [S-W]+Casamino acid+agar, colony was formed by anaerobic culture of feces. Then, the colony was cultivated in LBS medium [a selective medium for *Lactobacillus lactis*, consisting of trypticase 10 g, yeast extract 5 g, meat extract 10 g, $KH_2PO_4$ 6 g, ammonium hydrogen citrate 2 g, glucose 20 g, Tween 80 (trade name for Polyoxyethylene sorbitan monooleate) 1 g, sodium acetate 40 g, solution B 15 ml and glacial acetic acid (99.5%) 3.7 ml, which requires no pH-adjustment and no sterilization, the solution B being composed of $FeSO_4.7H_2O$ 0.5 g, $MnSO_4.nH_2O$ 2.47 g, NaCl 0.5 g, $MgSO_4.7H_2O$ 10 g and water 250 ml] and bacterial cells grown on the medium were collected. The cells were cultivated in a normal agar medium, and among the strains which grew only those strains which agreed accurately with the definition of *Lactobacillus lactis* were retained.

Then, the strains were classified according to variation in auxotrophy; by means of the following minimal nutrient mediums:

(a) glucose or starch, inorganic salts and water;

(b) An odoriferous compound containing sulfur, nitrogen or carbon, which is limited to one contained in feces, is added to (a);

(c) Vitamins are added individually or in combination, to (a);

(d) Amino acids are added individually or in combination, to (a);

(e) Specific vitamins are added individually or in combination, to (a);

(f) Tryptophane is added to (a);

(g) Amino acids containing sulfur are added individually or in combination, to (a).

In the above described medium, vitamins include vitamin A, vitamin $B_1$, vitamin $B_2$, vitamin $B_6$, vitamin $B_{12}$, nicotinamide, calcium panthothenate, vitamin C, vitamin $D_{12}$, etc., specific vitamins include vitamins other than the above described vitamins, such as folic acid, biotin, etc. Amino acids include ones other than specified amino acids and sulfur-containing amino acids, such as glycine, glutamic acid, lysine, alanine, phenylalanine, arginine, aspartic acid, etc., and specific amino acid include tryptophan. Sulfur-containing amino acids includes cystine, cysteine, methionine, taurine, etc.

*Streptococcus faecalis* used in the present invention is one which is usually added to feed stuffs for domestic animals. However, is must be a strain capable of producing an antibiotic, because the antibiotic produced suppresses the growth and multiplication of intestinal saprophytes and assists indirectly the multiplication of the Lactobacillus used in the present invention.

For the isolation of such *Streptococcus faecalis*, feces of man or domestic animals are used as the source for isolation and they are cultivated at abou 34° to about 39° C. under aerobic conditions in a selective medium for *Streptococcus faecalis*, such as SF medium consisting of peptone 20 g, glucose 5 g, $K_2HPO_4$ 4 g, $KH_2PO_4$ 1.5 g, $NaN_3$ 0.5 g, NaCl 5 g, BCP (Bromocresol Purple) 0.032 g, agar 15 g and water 1 l and having a pH of 6.9~7.2. The *Streptococcus faecalis* obtained is subjected to hemolysis testing to retain non-hemolytic ones, from which those having the ability to produce antibiotics are further retained. The strains thus retained are inoculated to a medium consisting of skimmed milk and sucrose. From the resulting bacterial cells, those having good odor and taste are selected and used in the present invention.

A representative testing procedure to determine whether the strain is one producing antibiotics comprises coating *Streptococcus faecalis* on an agar medium containing sugar and $CaCO_3$ in an amount of 10 mm of diameter, culturing at 37° C. for 48 to 72 hours, streaking a disease germ on the medium in a radiated state from the center of the cultured *Streptococcus faecalis* and continuing to culture for 24 to 48 hours to examine that the *Streptococcus faecalis* produces antibiotics.

The antibiotics formed by *Streptococcus faecalis* are aminoglucoside having lower heat-resistance, and 4 to about 5 kinds of antibiotics having a narrow spectrum of antimicrobial activity are formed from one strain. These 4 to about 5 kinds of antibiotics having a narrow spectrum of antimicrobial activity exhibit together the same property as a single antibiotic having a very wide spectrum of antimicrobial activity.

As regards the toxicity, *Streptococcus faecalis* is rather non-toxic, as compared with activity and metabolism of other intestinal bacteria, amounting up to 100 billions. As for the non-hemolytic *Streptococcus faecalis* strain producing antibiotics, it is considered that this strain rather assists the activity of Lactobacillus and Bifidobacterium and suppresses the activity of pathogenic bacteria.

Especially preferred strains of *Streptococcus faecalis* are those deposited at the Institute of Fermentation, Osaka, Japan under International Registration IFO Nos. 14452 and 14453.

As described above, at least one of *Lactobacillus deodorans, Lactobacillus clearans,* and a mixed strain of *Lactobacillus sulfurica* and *Lactobacillus nitrosus* is used in combination with the above-mentioned *Streptococcus faecalis* according to the present invention. The ratio of the combination of Lactobacillus to *Streptococcus faecalis* is 150 to about 0.01:1 by weight, preferably 100 to about 0.01:1, more preferably 30 to about 0.03:1 by weight. Above all, a ratio of about 10:1, which is the ratio of intestinal flora, is usually employed. For direct application to the mucosa of the skin, Lactobacillus is used in an amount less than that of Streptococcus, that is, in a ratio of Lactobacillus to Streptococcus of preferably 1 to about 0.03:1 by weight. In order to attain the same effect as *Lactobacillus clearans* by using *Lactobacillus sulfurica* and *Lactobacillus nitrosus*, it is sufficient to use a mixture of *Lactobacillus sulfurica* and *Lactobacillus nitrosus*, each present in the same amount as *Lactobacillus clearans*.

For preparing dry bacterial preparations of such Lactobacillus and *Streptococcus faecalis*, to which Bifidobacterium and/or Bacillus is further added if desired, it is sufficient to mix them together, preferably, in a ratio of 5 to about 15 parts by weight of Lactobacillus, 10 to about 100 parts by weight of Bifidobacterium and 0.05 to about 0.15 parts by weight of Bacillus to 1 part by weight of *Streptococcus faecalis*.

On using the above four Lactobacillus strains and *Streptococcus faecalis* in combination, according to the present invention, Bifidobacterium, Bacillus or a mixture of Bifidobacterium and Bacillus may also be used in combination therewith. Bifidobacterium is effective for maintaining the deodorant effect still after the administration is stopped, and Bacillus is effective for heightening the ability of Lactobacillus and Streptococcus in digesting offensively odoriferous substances for deodorization.

The Bifidobacterium used in the present invention may be either a Bifidobacterium strain which is usually used for the production of yogurt or that used for feed stuffs or food. In the present invention, strains deposited at ATCC were used.

As the Bacillus used in the present invention, *Bacillus coagulans* strains which are excellent as seed bacteria for yogurt, *Bacillus subtilis* strains which are excellent as bacteria for producing fermented soybeans, or the like are preferably used. Other Bacillus strains used for feed stuffs or food may also be employed.

The Bifidobacterium is used preferably in an amount of 1 to about 10 times by weight of the Lactobacillus used in the present invention, and the Bacillus in an amount of 1 to about 0.01 times by weight of the Lactobacillus used in the present invention.

It has been found that the ratio of individual strains obtained after cultivation of the strains used in the present invention correponds to the ratio of individual strains added originally to the culture medium. However, for the cultivation of several strains including Bifidobacterium, it is desirable to select a medium in which the Bifidobacterium grows well, as the medium for cultivating them simultaneously, so that the Bifidobacterium having a lower growth rate may begin multiplication sooner than other kinds of strains.

The deodorizers of the present invention are prepared mainly in the form of a live bacterial preparation, for example, by the following processes:

One process is (1) a process wherein the moisture content of the wet cells of the Lactobacillus used in the present invention and *Streptococcus faecalis* collected by centrifugation is reduced (preferably by weight), and the cells are mixed with excipients and dried in vacuum (preferably to a moisture content of about 2% by weight). Another process is (2) a process wherein wet cells of the Lactobacillus used in the present invention and *Streptococcus faecalis* collected by centrifugation are dispersed in a solution of excipients, and the resulting dispersion is freeze-dried and if necessary further mixed with dry excipients. Further, another process is (3) a process wherein preparations containing a single strain or a plurality of strains prepared by the above process (1) or (2) are mixed to obtain a preparation containing the proper amounts of individual strains.

Suitable excipients, include starch, lactose, sucrose, skimmed milk, dextrin, gelatin, calcium carbonate and an amino acid containing sulfur, used individually or as a mixture of two or more thereof. It is preferred to use an excipient in an amount of 1 to about 50 parts by weight per 1 part by weight of wet cells. When it is desired to use Bifidobacterium and/or Bacillus together with the above wet cells, the cells of Bifidobacterium and/or Bacillus are admixed so as to form an emulsion which gives a dry bacteria preparation having the effective ratio of the individual strains. It is preferred to use 5 to about 100 parts by weight of the Lactobacillus used in the present invention and 0.05 to about 0.15 parts by weight of Bifidobacterium and/or Bacillus per 1 part by weight of *Streptococcus faecalis*.

Suitable solutions or dispersions of excipient used in the above process (2) include solutions or dispersions of lactose, sucrose, skimmed milk, starch and the like.

In the above processes (1) to (3), at least one compound selected from the group of a sulfur-containing amino acids such as cystine, cysteine, methionine, taurine, etc., a specific amino acids, such as glutamic acid sodium glutamate, glycine, alanine, histidine, tyrosine, etc., or odoriferous compounds containing nitrogen atoms, sulfur atoms or carbon atoms are preferably included in an amount of 0.1 to 10 weight percent. The sulfur containing amino acid, the specific amino acid or the odoriferous compound are effective in preventing lowering of deodorizing ability of the deodorizer which is caused during culture or storage. In view of the effect, sulfur-containing amino acids are the most preferable. In the specific amino acids, it's effect becomes lower according to the order of glutamic acid, sodium glutamate, glycine, alanine, histidine and tyrosine.

The deodorizer of the present invention can be used for the preparation of a suppository and surgical absorbent cotton. Then it is preferable to convert the Lactobacillus and *Streptococcus faecalis* beforehand into resistant strains against disinfectants to be used. The suppository can be prepared by mixing the Lactobacillus and *Streptococcus faecalis* with isotonic sodium chloride solution in a ratio desired, for example, in a ratio of 10:1, letting the mixture stand for a suitable period, for example, for 5 minutes to 2 hours, and absorbing well the cotton with the mixture. For the preparation of surgical cotton absorbent, both strains are dried seperately and adhered to cotton successively, or both strains are mixed with isotonic sodium chloride solution and the cotton is dipped in the resulting mixture and dried. Of course, the methods of preparing the suppository or surgical absorbent cotton are not limited to those methods described above. However, it is preferable that the deodorizer is in the dried condition to restore its ability.

The deodorizers of the present invention can be used as valuable additives for feed stuffs and the like.

For addition to feed stuffs, the Lactobacillus and *Streptococcus faecalis* are cultivated at the same time in one medium in a desired ratio, for example, in a ratio of 10:1, and the culture solution is, after centrifugation, dried and used as an additive for feed stuffs, or the Lactobacillus and *Streptococcus faecalis* are cultivated separately to prepare dried cells, and the two kinds of dried cells are mixed together in a desired ratio, for example, in a ratio of 10:1, and used as an additive for feed stuffs. Since there is a difference in heat resistance between the Lactobacillus and *Streptococcus faecalis* (the latter being more resistant to heat, than the former), it is rather economical to employ the latter method for addition in producing the preparation.

Generally speaking, when the affinity for mucous membranes is taken into consideration, whether an aerobic strain is used or an anaerobic strain is used is determined by whether the mucous membrane to which the strain is applied exists under aerobic conditions or under anaerobic conditions. Although Lactobacillus and Streptococcus are representatives of bacteria having good affinity for mucous membranes, Streptococcus preferring aerobic conditions is suitable for application to the mucous membrane of the mouth and Lactobacillus capable of being active even under anaerobic conditions is suitable for application to the mucous membrane of the vaginal region.

However, when contaminant bacteria such as saprogens and pathogens were present in the vaginal region and the region related to the vagina (especially the vulva or pudenda), it was difficult in many cases to attain the desired effect by the use of Lactobacillus only. Although a process for reducing these contaminant bacteria beforehand by means of a disinfectant and using Lactobacillus resistant to the disinfectant was undertaken, it was still difficult to obtain the effect as desired, because the effect of the disinfectant did not endure for a long time.

The deodorizer of the present invention acts effectively particularly at such regions. Because of the effect of antibiotics formed by Streptococcus faecalis and of the high affinity to mucous membrane under aerobic conditions of Streptococcus faecalis, the Lactobacillus can exhibit its inherent properties effectively. Thus, the deodorizers of the present invention are valuable as suppositories and further as medicines for external use. It is preferable to administer a disinfectant beforehand and then apply the suppository or the medicines for external use of the present invention, to which resistance against the disinfectant is provided.

Thus, the deodorizers of the present invention exhibit an excellent effect, not only in intestinum but also in other mucosae especially at the pubic region.

Hereinafter, a method of isolating the Streptococcus used in the present invention is explained in detail. However, the invention is not to be construed as being limited to such method.

Isolation Method for Streptococcus faecalis (1) SF medium (consisting of peptone 20 g, glucose 5 g, $K_2HPO_4$ 4 g, $KH_2PO_4$ 1.5 g, $NaN_3$ 0.5 g, NaCl 5 g, BCP 0.032 g, agar 15 g and water 1 l and having a pH of 6.9 to about 7.2), which is a selective medium for Streptococcus faecalis, was employed as a culture medium. Feces of man and animals, were suspended in the SF medium and cultivated at 37° C. under aerobic conditions for 48 hours.

(2) Those cells which were recognized as Streptococcus faecalis by classification, were subjected to hemolysis testing and non-hemolytic cells were retained.

(3) The ability to produce antibiotics was tested and those having the ability of producing antibiotics were retained.

(4) Then, the strain retained was inoculated to a yogurt medium (consisting of skimmed milk 100 g and sucrose 100 g) and cultivated at 37° C. for 48 hours to prepare yogurt. The yogurt was subjected to odor and taste testing, and the cells having good odor and taste were retained.

The following example is exemplary of the collection of cells.

Collection of Cells from Culture Solution

In the cases of Lactobacillus clearans, Lactobacillus deodorans, Lactobacillus sulfurica and Lactobacillus nitrosus used in the present invention, Streptococcus faecalis and Bacillus, each strain was inoculated solely to the abovementioned MRS-lactose medium, i.e. a medium consisting of meat extract 10 g, peptone 10 g, yeast extract 5 g, lactose 20 g, Tween80 1 ml, $KH_2PO_4$ 2 g, sodium acetate 5 g, ammonium citrate 2 g, $MgSO_4 \cdot 7H_2O$ 0.2 g and $MnSO_4 \cdot 4H_2O$ 0.05 g, cultivation was effected at 37° C. for 72 hours, and the cells were collected using a refrigerated centrifuge.

In the case of Bifidobacterium, the strain was inoculated to the MRS-lactose medium to which 1 mg of vitamin $B_2$, 8 mg of calcium pantothenate and 0.1 mg of biotin were added, cultivation was effected at 37° C. for 96 hours, and the cells were collected using a refrigerated centrifuge.

The following examples are given to illustrate the present invention in greater detail. Unless otherwise indicated herein, all parts, percents, ratios and the like are by weight.

EXAMPLE 1

The degree of deodorization of $Na_2S \cdot 9H_2O$ and $NH_3$ using a mixture of Lactobacillus strain and Streptococcus faecalis was examined.

The following Lactobacillus strains and Streptococcus faecalis were inoculated to the medium comprising meat extract 5 g, peptone 5 g, glucose 1 g, $CaCO_3$ 1 g and feces 1 g, which contains $Na_2S \cdot 9H_2O$ 0.5 g or $NH_3$ 0.5 g, and cultivated to examine the degree of decrease of $Na_2S \cdot 9H_2O$ and $NH_3$. The results are shown in the following Table 1.

TABLE 1

| Lactobacillus | Str. faecalis | $Na_2S \cdot 9H_2O$ 500 ppm | | | $NH_3$ | 500 ppm | |
|---|---|---|---|---|---|---|---|
| | | 24 | 28 | 72 hrs. | 24 | 48 | 72 hrs. |
| Clearans | | | | | | | |
| 6587 | ⓐ | 390 | 280 | 220 ppm | 400 | 280 | 225 ppm |
| 6588 | ⓐ | 300 | 225 | 180 | 300 | 225 | 180 |
| 6589 | ⓐ | 300 | 225 | 180 | 330 | 225 | 190 |
| 6590 | ⓐ | 250 | 110 | 90 | 300 | 135 | 110 |
| Nitrosus | | | | | | | |
| 7385 | ⓐ | 510 | 510 | 530 | 400 | 280 | 225 |
| 7386 | ⓐ | 515 | 515 | 520 | 400 | 280 | 225 |
| Sulfurica | | | | | | | |
| 7383 | ⓐ | 400 | 280 | 220 | 520 | 580 | 610 |
| 7384 | ⓐ | 400 | 280 | 220 | 520 | 580 | 620 |
| Deodorans | | | | | | | |
| 1946 | ⓐ | 180 | 30 | 0 | 180 | 40 | 0 |
| 2742 | ⓐ | 140 | 20 | 0 | 140 | 40 | 0 |
| 2779 | ⓐ | 225 | 80 | 0 | 225 | 90 | 0 |
| 2780 | ⓐ | 225 | 80 | 0 | 225 | 90 | 0 |
| 2781 | ⓐ | 180 | 60 | 0 | 180 | 70 | 0 |
| 2782 | ⓐ | 225 | 70 | 0 | 225 | 85 | 0 |

For comparison, the same procedures were repeated except that the following Lactobacillus were solely used instead of the above mixture of Lactobacillus and Streptococcus faecalis. The results are shown in the following Table 2.

TABLE 2

| Lactobacillus | | Na$_2$S.9H$_2$O 500 ppm | | | NH$_3$ 500 ppm | | |
|---|---|---|---|---|---|---|---|
| | | 24 | 48 | 72 hrs | 24 | 48 | 72 hrs. |
| L. Clearans | 6587 | 400 | 300 | 250 ppm | 400 | 300 | 250 ppm |
| | 6588 | 300 | 250 | 200 | 350 | 250 | 200 |
| | 6589 | 300 | 250 | 200 | 350 | 250 | 200 |
| | 6590 | 250 | 125 | 100 | 300 | 150 | 125 |
| L. Nitrosus | 7385 | 510 | 515 | 525 | 400 | 300 | 250 |
| | 7386 | 515 | 520 | 525 | 400 | 300 | 250 |
| L. Sulfurica | 7383 | 400 | 300 | 250 | 515 | 590 | 625 |
| | 7384 | 400 | 300 | 250 | 530 | 650 | 650 |
| | 1946 | 200 | 50 | 0 | 200 | 50 | 0 |
| | 2742 | 150 | 30 | 0 | 150 | 50 | 0 |
| L. Deodorans | 2779 | 250 | 100 | 0 | 250 | 100 | 0 |
| | 2780 | 250 | 100 | 0 | 250 | 100 | 0 |
| | 2781 | 200 | 70 | 0 | 200 | 80 | 0 |
| | 2782 | 250 | 90 | 0 | 250 | 100 | 0 |

As is apparent from the Tables, the combined use of Lactobacillus and *Streptococcus faecalis* results in an increase of assimilating ability by 10 to 20% as compared with the sole use of Lactobacillus.

*Lactobacillus deodorans* is stronger in assimilating ability than *Lactobacillus clearans*. The former consumes Na$_2$S.9H$_2$O and NH$_3$ completely in 72 hours, and while, the latter can not consume them completely, *Lactobacillus nitrosus* and *Lactobacillus sulfurica* also can not consume them completely.

The strains used in the experiments are shown in Table 3 below:

TABLE 3

Strains used in Experiments

| Kind | Fermentation Research Institute | | Institute for Fermentation, Osaka | ATCC |
|---|---|---|---|---|
| | Domestic Registration FERM-P | International Registration FERM-BP | International Registration IFO | |
| Lactobacillus clearans | No. 6587 | | No. 14253 | |
| | No. 6588 | | | |
| | No. 6589 | | | |
| | No. 6590 | | No. 14254 | |
| | No. 1946 | | No. 14450 | |
| | No. 2742 | | | |
| Lactobacillus deodorans | No. 2779 | | No. 14451 | |
| | No. 2780 | | | |
| | No. 2781 | | | |
| | No. 2782 | | | |
| Lactobacillus nitrosus | No. 7385 | | No. 14257 | |
| | No. 7386 | | No. 14258 | |
| Lactobacillus sulfurica | No. 7383 | | No. 14255 | |
| | No. 7384 | | No. 14256 | |
| | No. 2082 (ⓑ strain) | | No. 14452 | |
| Streptococcus faecalis | No. 7382 (ⓐ strain) | | No. 14453 | |
| | | | | No. 6569(ⓒ strain) |
| Bifidobacterium | | | | No. 14506(ⓓ strain) |
| | | | | No. 11146(ⓐ strain) |
| | | | | No. 11863(ⓑ strain) |
| Bacillus | No. 2930 (A strain) | | | |
| | | | No. 3335 (B strain) | |

(Note)
Deposition numbers given on the same line show the identical strain. The abbreviated name used in this specification is given in the parentheses after the Registration number.
The a strain and b strain of *Streptococcus faecalis* produce antibiotics.

The ⓒ strain and ⓓ strain of *Streptococcus faecalis* do not produce antibiotics. The A strain of the Bacillus genus is a seed cell for yogurt (*Bacillus coagulans*). The B strain of the Bacillus genus is a seed cell for fermented soybeans (*Bacillus subtilis*).

The following experiments were effected using IFO Nos. 14253 and 14450, as *Lactobacillus clearans* and *Lactobacillus deodorans*, respectively.

EXAMPLE 2

To 1 g of fresh human feces was added 9 ml of isotonic sodium chloride solution. To (1) one mixture so obtained 1 ml of a cultured cell solution of *Lactobacillus clearans* was added, and to (2) another mixture 1 ml of a cultured cell solution of *Lactobacillus clearans* plus 0.5 ml of a cultured cell solution of ⓐ strain were added, and then the mixtures were allowed to stand at 37° C. for 48 hours.

By judgement of odor, it was noted that the degree of deodorization was higher in the group of experiments of the case of mixture (2) and the amount of feces not deodorized was reduced by half as compared with the case of mixture (1), although the feces was not deodorized in two instances of ten instances of the latter case tested.

By oral administration of *Lactobacillus clearans* only and of *Lactobacillus clearans* plus ⓐ strain, it was recognized as the degree of deodorization was examined with respect to the feces excreted, that the deodorant effect was higher and instances of lack of deodorization were less, in the cases wherein *Lactobacillus clearans* plus a strain were administered.

These experiments (in vivo) show that *Lactobacillus clearans* as well as *Lactobacillus clearans* plus ⓐ strain are effective in intestines where feces (containing saprogens, most of which are anaerobic, amounting upto $1.5 \times 10^{11}$ cells/g of faecalis) are present. Although a considerable effect was noticed by contact of either of *Lactobacillus clearans* and *Lactobacillus clearans* plus ⓐ strain, the combination of *Lactobacillus clearans* plus ⓐ was more effective, as expected, compared with *Lactobacillus clearans* only. Here, the effect means that a high degree of deodorization was attained and instances of lack of deodorization were reduced.

Although the above experiments were those relating to *Lactobacillus clearans*, the same comparative experiments as these experiments were effected with respect to *Lactobacillus deodorans* and to *Lactobacillus sulfurica* plus *Lactobacillus nitrosus*, using IFO Nos. 14255, 14256, 14453. That is, comparative experiments between *Lactobacillus deodorans* and *Lactobacillus deodorans* plus ⓐ strain and those between *Lactobacillus sulfurica* plus *Lactobacillus nitrosus* and *Lactobacillus sulfurica* plus *Lactobacillus nitrosus* plus ⓐ strain were effected.

The same tendency as in *Lactobacillus clearans* was observed in *Lactobacillus sulfurica* plus *Lactobacillus nitrosus*.

The effect of ⓐ strain was larger and more significant in the case of *Lactobacillus deodorans*. That is, the use of ⓐ strain, a *Streptococcus faecalis* strain producing antibiotics, showed a very significant effect against offensive odor not only by oral administration but also by application to the female pubic region.

The results obtained are shown in Example 6.

EXAMPLE 3 (PREPARATION OF BIODEODORIZER)

Preparation of Yogurt (1) Preparation of yogurt by fermentation of *Lactobacillus clearans* and *Streptococcus faecalis*

A medium for seed cells (containing 30 g of skimmed milk and 3 g of calcium carbonate and having a pH of 7.0) was divided into two and sterilized. Then, the above strains were inoculated to each medium, respectively, and cultivated at 37° C. for 24 hours to obtain seed cells of *Lactobacillus clearans* and seed cells of *Streptococcus faecalis*. (The number of cells was $1.5 \times 10^9$ cells/ml for *Lactobacillus clearans* and $2 \times 10^9$ cells/ml for *Streptococcus faecalis*.)

On the other hand, 200 ml of a medium for yogurt consisting of skimmed milk 100 g, sucrose 100 g and agar 2 g, was sterilized.

To the medium for yogurt so obtained, 10 ml of the seed cells of *Lactobacillus clearans* and 0.8 ml of the seed cells of *Streptococcus faecalis* were added. Then, cultivation was effected at 37° C. for 24 hours to prepare yogurt.

The yogurt prepared contained $2.5 \times 10^9$ cells/ml of *Lactobacillus clearans* and $2.5 \times 10^8$ cells/ml of *Streptococcus faecalis*. The ratio of *Lactobacillus clearans* to *Streptococcus faecalis* was 10:1 (by weight). This yogurt was administered to man and animals.

(2) Preparation of yogurt by fermentation of *Lactobacillus clearans*, *Streptococcus faecalis* and Bifidobacterium Seed cells of *Lactobacillus clearans* and *Streptococcus faecalis* were obtained by preparing a medium for seed cells, inoculating each strain to the medium and cultivating at 37° C. for 24 hours. Separately, Bifiobacterium was inoculated to a medium for seed cells consisting of skimmed milk 30 g cysteine 1 g, Vitamin $B_2$ 1 mg, calcium pantothenate 8 mg and biotin 0.1 mg, and cultivated at 37° C. for 72 hours.

On the other hand, 200 ml of a medium for yogurt consisting of skimmed milk 100 g, sucrose 100 g, agar 2 g and cystein 1 g, was sterilized and subjected to sterile filtration. Then, 1 mg of vitamin $B_2$, 8 mg of calcium pantothenate and 0.1 mg of biotin were added to the medium.

To the medium thus obtained, 10 ml of the seed cells of Bifidobacterium was added, and cultivation was effected at 37° C. for 36 hours.

Then, 10 ml of the seed cells of *Lactobacillus clearans* and 0.8 ml of the seed cells of *Streptococcus faecalis* were further added simultaneously to the culture medium, and cultivation was further continued at 37° C. for 36 hours to prepare yogurt.

The yogurt thus prepared contained $2 \times 10^9$ cells/ml of *Lactobacillus clearans*, $2 \times 10^8$ cells/ml of *Streptococcus faecalis* and $3 \times 10^9$ cells/ml of Bifidobacterium. The ratio of *Lactobacillus clearans*:*Streptococcus faecalis*:Bifidobacterium = 10:1:15 (by weight).

EXAMPLE 4 (PREPARATION OF BIODEODORIZER)

Preparation of Wet Cell Preparations

To MRS-lactose medium consisting of meat extract 10 g, peptone 10 g, yeast extract 5 g, lactose 20 g, Tween 80 1 ml, $KH_2PO_4$ 2 g, sodium acetate 5 g, ammonium citrate 2 g, $MgSO_2.7H_2O$ 0.2 g and $MnSO_4.4H_2O$ 0.05 g, *Lactobacillus clearans*, *Streptococcus faecalis* and Bacillus were inoculated separately, and pure cultivation of each strain was effected at 37° C. for 72 hours. After completion of the cultivation, cells were collected by centrifugation. (The yield was 1 g for *Lactobacilus clearans*, 1.2 g for *Streptococcus faecalis* and 1 g for Bacillus, per 100 ml.) In the case of Bifidobacterium, cysteine 1 g, vitamin $B_2$ 1 mg, calcium pantothenate 8 mg and biotin 0.1 mg were added to MRS-lactose medium and the cultivation was effected at 37° C. for 96 hours. After completion of cultivation, cells were collected by centrifugation. (The yield was 0.5 g per 1000 ml.)

(a) Preparations containing *Lactobacillus clearans* and *Streptococcus faecalis*

By mixing 10 g of the above collected cells of *Lactobacillus clearans* with 1 g of those of *Streptococcus faecalis*, a preparation was formed. The preparation was admixed with a feed stuff. (For chickens, 0.5 g of the preparation was added to 1 kg of the feed stuff, and for pigs, 0.8 g of the preparation was added to 1 kg of the feed stuff.)

(b) Preparations containing *Lactobacillus clearans*, *Streptococcus faecalis* and Bacillus By mixing 10 g of the above collected cells of *Lactobacillus clearans*, 1 g of those of *Streptococcus faecalis* and 100 g of those of Bifidobacterium together, a preparation was formed. The preparation was admixed with a feed stuff (for example, in an amount of 0.6 g per 1 kg of a feed stuff for chickens, and in an amount of 1 g per 1 kg of a feed stuff for pigs).

(c) Preparations containing *Lactobacillus clearans*, *Streptococcus faecalis*, Bifidobacterium and Bacillus By mixing 10 g of the above collected cells of *Lactobacillus clearans*, 1 g of those of *Streptococcus faecalis*, 100 g of those of Bifidobacterium and 0.5 g of those of Bacillus together, a preparation was formed. The preparation was added to a feed stuff (for example, in an amount of 0.6 g per 1 Kg of a feed stuff for chickens and in an amount of 1 g per 1 kg of a feed stuff for pigs).

Preparation of Dry Cell Preparations (1) Semi-dry Cell Preparations

To the above-described MRS-lactose medium and the above-described medium for Bifidobacterium, *Lactobacillus clearans, Streptococcus faecalis* and Bifidobacterium were inoculated individually, and pure cultivation of each strain was effected. To 10 g of each of the wet cells collected by centrifugation 300 g of starch dried by heating to have a moisture content of 0.2% and 1 g of cystine were added and mixed to form a wet preparation having finally a moisture content of 2% or less.

(a) Preparations containing *Lactobacillus clearans* and *Streptococcus faecalis*

By mixing 10 g of the *Lactobacillus clearans* thus dried and coated, with 1 g of the *Streptococcus faecalis* thus dried and coated, a semi-dry preparation was formed. The preparation was put into a vial, sealed under nitrogen gas and stored in a cold and dark place.

(b) Preparations containing *Lactobacillus clearans, Streptococcus faecalis* and Bifidobacterium By mixing 10 g of the *Lactobacillus clearans* thus dried and coated, 1 g of the *Streptococcus faecalis* dried and coated and 100 g of the Bifidobacterium dried and coated, together, a semi-dry preparation was formed. The preparation was put into a vial, sealed under nitrogen gas and stored in a cold and dark place.

(2) Dry Cell Preparations

To the above-described MRS-lactose medium and the above-described medium for Bifidobacterium, *Lactobacillus clearans, Streptococcus faecalis* and Bifidobacterium were individually inoculated, and pure cultivation of each strain was effected. Ten g of each of the wet cells collected by centrifugation was dispersed in 100 ml of a solution containing 1% of lactose and 0.1% of cystine, and the solution was then freeze-dried.

(a) Preparations containing *Lactobacillus clearans* and *Streptococcus faecalis*

By mixing 10 g of the live cell preparation thus obtained of *Lactobacillus clearans* with 1 g of the live cell preparation thus obtained of *Streptococcus faecalis*, a dry cell preparation was formed. The preparation was filled in a capsule and stored.

(b) Preparations containing *Lactobacillus clearans, Streptococcus faecalis* and Bifidobacterium By mixing 10 g of the *Lactobacillus clearans* obtained above, 1 g of the *Streptococcus faecalis* obtained above and 100 g of the Bifidobacterium obtained above, together, a dry cell preparation was formed. The preparation was processed into tablets and stored in a vial.

EXAMPLE 5

Procedures (1) Mixed culture of *Lactobacillus clearans, Lactobacillus deodorans* or an equally mixed strain of *Lactobacillus sulfurica* and *Lactobacillus nitrosus* and/or Bacillus genus was effected using a medium consisting of skimmed milk 100 g, sucrose 100 g and agar 2 g. First, the medium was sterilized at 100° C. for 30 minutes, intermittently for 3 days. Then, the above strains were inoculated to the medium simultaneously in a desired cell number ratio, and culture was effected at 37° C. for 24 hours to prepare a product.

(2) Mixed culture of the strains used in (1) above with Bifidobacterium was effected in the above-mentioned medium to which cystine 1 g, vitamin $B_2$ 1 mg, calcium pantothenate 8 mg and biotin 0.1 mg were added under sterile conditions, Bifidobacterium was cultivated previously at 37° C. for 36 hours, and then the other strains were inoculated simultaneously and the cultivation was continued further at 37° C. for 36 hours to prepare a product.

(3) The product thus prepared was administered to patients twice a day, at morning and evening, for a continuous 4 days.

The results of the deodorization test are shown in Table 4, Table 5 and Table 6. Table 4 shows the results of testing wherein *Lactobacillus clearans* was used as the Lactobacillus strain. Table 5 shows the results of testing using *Lactobacillus deodorans*, and Table 6 using an equally mixed strain of *Lactobacillus sulfurica* and *Lactbacillus nitrosus*, as the Lactobacillus strain.

TABLE 4

| | | Effect of Combined Use with *Lactobacillus Clearans* | | | | | | | | | | | | |
|---|---|---|---|---|---|---|---|---|---|---|---|---|---|---|
| | Number of Strains used (in total with Lactobacillus | *Streptococcus faecalis* | | | | *Bifidobacterium* | | Bacillus | | Deodorant Effect | | | | |
| Experiment No. | clearans) | a | b | c | d | α | β | A | B | Rate | Strength | Period | Feeing | Total |
| 1 | | + | | | | | | | | ◎ | ◎ | ◎ | ◎ | ◎ |
| 2 | | | + | | | | | | | ◎ | ◎ | Δ | Δ | ○ |
| 3 | | | | + | | | | | | Δ | Δ | Δ | Δ | Δ |
| 4 | 2 | | | | + | | | | | Δ | Δ | Δ | Δ | Δ |
| 5 | | | | | | + | | | | Δ | Δ | Δ | Δ | Δ |
| 6 | | | | | | | + | | | Δ | Δ | Δ | Δ | Δ |
| 7 | | | | | | | | + | | Δ | Δ | Δ | Δ | Δ |
| 8 | | | | | | | | | + | Δ | Δ | Δ | Δ | Δ |
| 9 | | + | | | | + | | | | ◎ | ◎ | ◎ | ◎ | ◎ |
| 10 | | + | | | | | + | | | ◎ | ◎ | ◎ | ◎ | ◎ |
| 11 | 3 | + | | | | | | + | | ◎ | ◎ | Δ | Δ | ○ |
| 12 | | + | | | | | | | + | ◎ | ◎ | Δ | Δ | ○ |
| 13 | | | + | | | + | | | | ◎ | ◎ | Δ | ○ | ○ |
| 14 | | | + | | | | + | | | ◎ | ◎ | Δ | Δ | ○ |
| 15 | | | + | | | | | + | | ◎ | ◎ | Δ | Δ | ○ |
| 16 | | | + | | | | | | + | ◎ | ◎ | Δ | Δ | ○ |
| 17 | 3 | | | + | | + | | | | Δ | Δ | Δ | Δ | Δ |
| 18 | | | | + | | | + | | | Δ | Δ | Δ | Δ | Δ |
| 19 | | | | + | | | | + | | Δ | Δ | Δ | Δ | Δ |

TABLE 4-continued

Effect of Combined Use with *Lactobacillus Clearans*

| Experiment No. | Number of Strains used (in total with *Lactobacillus clearans*) | *Streptococcus faecalis* a | b | c | d | *Bifido-bacterium* α | β | Bacillus A | B | Deodorant Effect Rate | Strength | Period | Feeing | Total |
|---|---|---|---|---|---|---|---|---|---|---|---|---|---|---|
| 20 |  |  |  | + |  |  |  |  | + | Δ | Δ | Δ | Δ | Δ |
| 21 |  |  |  | + | + | + |  |  |  | Δ | Δ | Δ | Δ | Δ |
| 22 |  |  |  | + |  |  | + |  |  | Δ | Δ | Δ | Δ | Δ |
| 23 |  |  |  | + |  |  |  | + |  | Δ | Δ | Δ | Δ | Δ |
| 24 |  |  |  | + |  |  |  |  | + | Δ | Δ | Δ | Δ | Δ |
| 25 |  |  |  |  |  | + | + |  |  | Δ | Δ | Δ | Δ | Δ |
| 26 |  |  |  |  |  | + |  |  | + | Δ | Δ | Δ | Δ | Δ |
| 27 |  |  |  |  |  |  | + | + |  | Δ | Δ | Δ | Δ | Δ |
| 28 |  |  |  |  |  |  | + |  | + | Δ | Δ | Δ | Δ | Δ |
| 29 |  | + |  |  |  | + |  | + |  | ◎ | ◎ | ◎ | Δ | ○ |
| 30 | 4 | + |  |  |  | + |  |  | + | ◎ | ◎ | Δ | ◎ | ○ |
| 31 |  | + |  |  |  |  | + | + |  | ◎ | ◎ | ◎ | Δ | ○ |
| 32 |  | + |  |  |  |  | + |  | + | ◎ | ◎ | ◎ | Δ | ○ |
| 33 |  |  | + |  |  | + |  | + |  | ◎ | ◎ | ◎ | Δ | ○ |
| 34 |  |  | + |  |  | + |  |  | + | ◎ | ◎ | Δ | Δ | ○ |
| 35 |  |  | + |  |  |  | + | + |  | ◎ | ◎ | Δ | Δ | ○ |
| 36 | 4 |  | + |  |  |  | + |  | + | ◎ | ◎ | Δ | Δ | ○ |
| 37 |  |  |  | + |  | + |  | + |  | Δ | Δ | Δ | Δ | Δ |
| 38 |  |  |  | + |  | + |  |  | + | Δ | Δ | Δ | Δ | Δ |
| 39 |  |  |  | + |  |  | + | + |  | Δ | Δ | Δ | Δ | Δ |
| 40 |  |  |  | + |  |  | + |  | + | Δ | Δ | Δ | Δ | Δ |
| 41 |  |  |  |  | + | + |  | + |  | Δ | Δ | Δ | Δ | Δ |
| 42 |  |  |  |  | + | + |  |  | + | Δ | Δ | Δ | Δ | Δ |
| 43 |  |  |  |  | + |  | + | + |  | Δ | Δ | Δ | Δ | Δ |
| 44 |  |  |  |  | + |  | + |  | + | Δ | Δ | Δ | Δ | Δ |

(The symbol "+" means "use in combination")
(The deposited Numbers of the strains used are shown in Example 1.)

Deodorant Effects

The deodorant effects shown in Tables 4, 5 and 6 are those evaluated as to the following four items:

(1) Whether the deodorant effect appeared rapidly or not, i.e. "rate".

(2) Whether the deodorant power was strong or not, i.e. "strength".

(3) For how many days did deodorant effect continue, i.e. "period".

(4) Whether the feeling on evacuation was good or not, i.e. "feeling".

With regard to each of the above items, when more than half of the patients judged that the effect was a remarkable one, the symbol ◎ was used. When more than half of the patients judged that the effect was present, the symbol ○ was used. When more than half of the patients judged that there was no effect, the symbol Δ was used.

Explanation of Table 4

The effect of the combined use of *Lactobacillus clearans* with the other strains is shown in Table 4.

I Combined Use of Two Kinds of Strains (1) Either of ⓐ strain and ⓑ strain produced plural antibiotics very well, though there was difference between these two strains in growth rate and ⓐ strain was superior to the ⓑ strain in rate. Both the ⓒ strain and ⓓ strain did not produce antibiotics, though their rate of growth and multiplying was superior than that of the ⓑ strain.

Experiment No. 1: The deodorant effect of *Lactobacillus clearans* plus the ⓐ strain was faster and stronger than that of the single use of *Lactobacillus clearans*. Also the duration time of the effect was somewhat longer than the time for the single use, and two-thirds of the patients expressed a good feeling on evacuation.

Experiment No. 2: The deodorant effect of *Lactobacillus clearans* plus the ⓑ strain was stronger than that of *Lactobacillus clearans* only. However, no lengthening of the duration was recognized with the combined use.

Experiments Nos. 3 and 4: The deodorant effect of *Lactobacillus clearans* plus the ⓒ strain or *Lactobacillus clearans* plus the ⓓ strain was noted to be almost the same as that of the *Lactobacillus clearans* only.

As is apparent from the above Experiments Nos. 1–4, the deodorant effect of *Lactobacillus clearans* is improved by the combined use with *Streptococcus faecalis* capable of producing antibiotics, although no improvement was brought about by the combined use with *Streptococcus faecalis* not capable of producing antibiotics.

(2) Experiments Nos. 5 and 6: In the case of *Lactobacillus clearans* plus the ⓐ strain or *Lactobacillus clearans* plus the ⓑ strain, lengthening of the deodorant period as compared with the single use of *Lactobacillus clearans* was noted by one-third of the patients subjected to the test. However, thus lengthening was not recognized by two-thirds of them.

In view of the past experience in biological testing, it can be said that such results of effectiveness amounting to 30% or so show that the combined is quite useful.

(3) The A strain is a *Bacillus coagulans* and has an excellent property as a seed cell for yogurt (see U.S. Pat. No. 4,210,672). The B strain is a *Bacillus subtilis* and has an excellent property as a seed cell for fermented soybeans. It is commercialy available.

Experiments Nos. 7 and 8: In the case of *Lactobacillus clearans* plus the A strain or *Lactobacillus clearans* plus, the B strain, no report that the deodorant effect was stronger or the deodorant period was longer, than the single use of *Lactobacillus clearans*, was received. The results of examination by gas chromatography also did not show any significant difference from the single use of *Lactobacillus clearans.*

II COMBINED USE OF THREE KINDS OF STRAINS (1) Combined use with *Streptococcus faecalis* producing antibiotics and Bifidobacterium From the experimental results, the effect attained by using the ⓐ strain was considered almost the same as that attained by using the ⓑ strain (though the a strain was somewhat superior to the ⓑ strain). Therefore, consideration about the experimental results obtained by using the ⓑ strain is omitted from the following explanation.

Experiments Nos. 9 and 10: In the case of the combined use of *Lactbacillus clearans* with the ⓐ strain and the ⓐ strain or the ⓑ strain, almost 70% of the test subjects reported that the effect was stronger and continued longer than the case of *Lactobacillus clearans* only and the feeling on evacuation was not unpleasant. Among those people who recognized thus effects, 20% reported that the combined use of these three strains was more effective than the combined use of Experiment No. 1 (*Lactobacillus clearans* plus the ⓐ strain), 30% reported that there was no difference from the combined use of Experiment No. 1 and the remaining 50% reported that the combined use of the three strains was rather inferior to the combined use of Experiment No. 1. The effect was mild and continued for a long time.

Experiments Nos. 17, 18, 21 and 22: In the case of combined use of *Lactobacillus clearans* with the ⓒ strain or the ⓓ strain and the ⓐ strain or the ⓑ strain, the effect was the same as the cases of Experiments Nos. 3 and 4. No report that the deodorant effect was strengthened or the period was lengthened was received.

From the results of the experiments as described above, 50% of the test subjects reported that when Bifidobacterium was added to *Lactobacillus clearans* and *Streptococcus faecalis* producing antibiotics, the deodorant effect attained was superior to the single use of *Lactobacillus clearans.*

Further, 50% of the test subjects reported that the effect of the combined use of these three strains was the same as, or better than, that of the combined use of *Lactobacillus clearans* with *Streptococcus faecalis* producing antibiotics. Only 15% of the test subjects reported that the combined use of the two strains was better than that of the three strains.

The combined use with *Streptococcus faecalis* not producing antibiotics was found to be not so effective.

(2) Combined use with *Streptococcus faecalis* producing antibiotics and Bacillus Experiments Nos. 11 and 12: In the case of the combined use of *Lactobacillus clearans* with the ⓐ strain and the A strain or the B strain, the deodorant effect was stronger than the single use of *Lactobacillus clearans* for more than 50% of the test subjects. In some test subjects, however, the effect was less than that attained by the combined use of *Lactobacillus clearans* and the ⓐ strain or of *Lactobacillus clearans*, the ⓐ strain and the ⓐ or the ⓑ strain.

Experiments Nos. 19 and 20: Neither combination was effective.

From the experimental results, it was found that the deodorant effect attained by adding a digestive Bacillus genus to *Lactobacillus clearans* and *Streptococcus faecalis* producing antibiotics was similar to that attained without such addition.

Further, the combined use with *Streptococcus faecalis* not producing antibiotics was found to be not so effective.

(3) Combined use with Bifidobacterium and Bacillus

Experiments Nos. 25, 26, 27 and 28: In either combination, almost 40% of the test subjects recognized a lengthening of the deodorant period. About 20% of those test subjects who recognized the lengthening reported that the strength was however weak, compared with the single use of *Lactobacillus clearans.*

[III] Combined use of four kinds of strains (1) Combined use with *Streptococcus faecalis,* Bifidobacterium and Bacillus Experiments Nos. 29, 30, 31 and 32: In the case of the combined use of *Lactobacillus clearans* with the ⓐ strain, the ⓐ strain or the ⓑ strain and the A strain or the B strain, the deodorant effect was sometimes rather weak compared with the case of the combined use of *Lactobacillus clearans* and the ⓐ strain. However, the period of duration was longest in the case of the combined use of these four kinds of strains.

Experiments Nos. 37, 38, 39, 40, 41, 42, 43 and 44: In the case of the combined use of *Lactobacillus clearans* with *Streptococcus faecalis* not producing antibiotics, Bifidobacterium and Bacillus, the deodorant effect was not superior to the single use of *Lactobacillus clearans.* From the results of these experiments, it was found that, by addition of Bifidobacterium and Bacillus to *Lactobacillus clearans* and *Streptococcus faecalis* producing antibiotics, a mild deodorant effect continued for the longest period although a remarkable change was not recognized in other respects, as compared with the cases in which Bifidobacterium and Bacillus were not added.

CONCLUSIONS

Summarizing the effects attained by the combined use of *Lactobacillus clearans* with various strains, it is apparent from the above results that combinations of (1) *Lactobacillus clearans* and *Streptococcus faecalis* producing antibiotics, (2) *Lactobacillus clearans, Streptococcus faecalis* producing antibiotics, and Bifidobacterium, (3) *Lactobacillus clearans, Streptococcus faecalis* producing antibiotics, and Bacillus, and (4) *Lactobacillus clearans, Streptococcus faecalis* producing antibiotics, Bifidobacterium and Bacillus, show better and/or longer deodorant effects, compared with the single use of *Lactobacillus clearans.*

TABLE 5

Effect of Combined Use with *Lactobacillus deodorans*

| Experiment No. | Number of Strains used (in total with *Lactobacillus deodorans*) | Streptococcus faecalis ⓐ | ⓑ | ⓒ | ⓓ | Bifidobacterium ⓐ | β | Bacillus A | B | Rate | Strength | Period | Feeling | Total |
|---|---|---|---|---|---|---|---|---|---|---|---|---|---|---|
| 1 | | + | | | | | | | | ◉ | ◉ | ○ | ○ | ◉ |
| 2 | | + | | | | | | | | ◉ | ◉ | ○ | ○ | ○ |
| 3 | | | + | | | | | | | △ | △ | △ | △ | △ |
| 4 | 2 | | | + | | | | | | △ | △ | △ | △ | △ |
| 5 | | | | | | + | | | | △ | △ | △ | △ | △ |
| 6 | | | | | | | + | | | △ | △ | △ | △ | △ |
| 7 | | | | | | | | + | | △ | △ | △ | △ | △ |
| 8 | | | | | | | | | + | △ | △ | △ | △ | △ |
| 9 | | + | | | | + | | | | ◉ | ◉ | ◉ | ◉ | ◉ |
| 10 | | + | | | | | + | | | ◉ | ◉ | ◉ | ◉ | ◉ |
| 11 | 3 | + | | | | | | + | | ◉ | ◉ | ○ | ○ | ◉ |
| 12 | | + | | | | | | | + | ◉ | ◉ | ○ | ○ | ◉ |
| 13 | | | + | | | + | | | | ◉ | ◉ | ◉ | ○ | ○ |
| 14 | | | + | | | | + | | | ◉ | ◉ | ○ | ○ | ○ |
| 15 | | | + | | | | | + | | ◉ | ◉ | ○ | ○ | ○ |
| 16 | | | + | | | | | | + | ◉ | ◉ | ○ | ○ | ○ |
| 17 | | | + | + | | | | | | △ | △ | △ | △ | △ |
| 18 | 3 | | | + | | | + | | | △ | △ | △ | △ | △ |
| 19 | | | | + | | | | + | | △ | △ | △ | △ | △ |
| 20 | | | | + | | | | | + | △ | △ | △ | △ | △ |
| 21 | | | | | + | + | | | | △ | △ | △ | △ | △ |
| 22 | | | | | + | | + | | | △ | △ | △ | △ | △ |
| 23 | | | | | + | | | + | | △ | △ | △ | △ | △ |
| 24 | | | | | + | | | | + | △ | △ | △ | △ | △ |
| 25 | | | | | | + | | + | | △ | △ | △ | △ | △ |
| 26 | | | | | | + | | | + | △ | △ | △ | △ | △ |
| 27 | | | | | | | + | + | | △ | △ | △ | △ | △ |
| 28 | | | | | | | + | | + | △ | △ | △ | △ | △ |
| 29 | | + | | | | + | + | | | ◉ | ◉ | ◉ | ◉ | ◉ |
| 30 | 4 | + | | | | + | | | + | ◉ | ◉ | ◉ | ◉ | ◉ |
| 31 | | + | | | | | + | + | | ◉ | ◉ | ◉ | ○ | ◉ |
| 32 | | + | | | | | + | | + | ◉ | ◉ | ◉ | ○ | ○ |
| 33 | | | + | | | + | + | | | ◉ | ◉ | ◉ | ○ | ○ |
| 34 | | | + | | | + | | | + | ◉ | ◉ | ◉ | ○ | ○ |
| 35 | | | + | | | | + | + | | ◉ | ◉ | ○ | ○ | ○ |
| 36 | | | + | | | | + | | + | ◉ | ◉ | ○ | ○ | ○ |
| 37 | | | | + | | + | + | | | △ | △ | △ | △ | △ |
| 38 | 4 | | | + | | + | | | + | △ | △ | △ | △ | △ |
| 39 | | | | + | | | + | + | | △ | △ | △ | △ | △ |
| 40 | | | | + | | | + | | + | △ | △ | △ | △ | △ |
| 41 | | | | | + | + | | + | | △ | △ | △ | △ | △ |
| 42 | | | | | + | + | | | + | △ | △ | △ | △ | △ |
| 43 | | | | | + | | + | + | | △ | △ | △ | △ | △ |

TABLE 6

Effect of combined use with *Lactobacillus sulfurica* plus *Lactobacillus nitrosus*

| Experiment No. | Number of Strains used (in total with *Lactobacillus sulfurica* plus *Lactobacillus nitrosus*) | Streptococcus faecalis ⓐ | ⓑ | ⓒ | ⓓ | Bifidobacterium ⓐ | β | Bacillus A | B | Rate | Strength | Period | Feeling | Total |
|---|---|---|---|---|---|---|---|---|---|---|---|---|---|---|
| 1 | | + | | | | | | | | ◉ | ◉ | ◉ | ◉ | ◉ |
| 2 | | | + | | | | | | | ◉ | ◉ | △ | △ | ◉ |
| 3 | | | | + | | | | | | △ | △ | △ | △ | △ |
| 4 | 2 | | | | + | | | | | △ | △ | △ | △ | △ |
| 5 | | | | | | + | | | | △ | △ | △ | △ | △ |
| 6 | | | | | | | + | | | △ | △ | △ | △ | △ |
| 7 | | | | | | | | + | | △ | △ | △ | △ | △ |
| 8 | | | | | | | | | + | △ | △ | △ | △ | △ |
| 9 | | + | | | | + | | | | ◉ | ◉ | ◉ | ◉ | ◉ |
| 10 | | + | | | | | + | | | ◉ | ◉ | ◉ | ◉ | ◉ |
| 11 | | + | | | | | | + | | ◉ | ◉ | △ | △ | ○ |
| 12 | 3 | + | | | | | | | + | ◉ | ◉ | △ | △ | ○ |
| 13 | | | + | | | + | | | | ◉ | ◉ | ◉ | ○ | ○ |
| 14 | | | + | | | | + | | | ◉ | ◉ | △ | △ | ○ |
| 15 | | | + | | | | | + | | ◉ | ◉ | △ | △ | ○ |
| 16 | | | + | | | | | | + | ◉ | ◉ | △ | △ | ○ |
| 17 | | | | + | | + | | | | △ | △ | △ | △ | △ |
| 18 | 3 | | | | + | | + | | | △ | △ | △ | △ | △ |

TABLE 6-continued

Effect of combined use with *Lactobacillus sulfurica* plus *Lactobacillus nitrosus*

| Experiment No. | Number of Strains used (in total with Lactobacillus sulfurica plus Lactobacillus nitrosus) | Streptococcus faecalis | | | | Bifido-bacterium | | Bacillus | | Deodorant Effect | | | | |
|---|---|---|---|---|---|---|---|---|---|---|---|---|---|---|
| | | ⓐ | ⓑ | ⓒ | ⓓ | α | β | A | B | Rate | Strength | Period | Feeling | Total |
| 19 | | | | + | | | | + | | Δ | Δ | Δ | Δ | Δ |
| 20 | | | | + | | | | | + | Δ | Δ | Δ | Δ | Δ |
| 21 | | | | | + | + | | | | Δ | Δ | Δ | Δ | Δ |
| 22 | | | | | + | | + | | | Δ | Δ | Δ | Δ | Δ |
| 23 | | | | | + | | | + | | Δ | Δ | Δ | Δ | Δ |
| 24 | | | | | + | | | | + | Δ | Δ | Δ | Δ | Δ |
| 25 | | | | | | + | | + | | Δ | Δ | Δ | Δ | Δ |
| 26 | | | | | | + | | | + | Δ | Δ | Δ | Δ | Δ |
| 27 | | | | | | | + | + | | Δ | Δ | Δ | Δ | Δ |
| 28 | | | | | | | + | | + | Δ | Δ | Δ | Δ | Δ |
| 29 | | + | | | | + | | + | | ◎ | ◎ | ◎ | ○ | ◎ |
| 30 | 4 | + | | | | + | | | + | ◎ | ◎ | ○ | Δ | ○ |
| 31 | | + | | | | | + | + | | ◎ | ◎ | ○ | Δ | ○ |
| 32 | | + | | | | | + | | + | ◎ | ◎ | ◎ | ○ | ○ |
| 33 | | | + | | | + | | + | | ◎ | ◎ | Δ | Δ | ○ |
| 34 | | | + | | | + | | | + | ◎ | ◎ | Δ | Δ | ○ |
| 35 | | | + | | | | + | + | | ◎ | ◎ | ○ | Δ | ○ |
| 36 | | | + | | | | + | | + | ◎ | ◎ | Δ | Δ | ○ |
| 37 | | | | + | | + | | + | | Δ | Δ | Δ | Δ | Δ |
| 38 | 4 | | | + | | + | | | + | Δ | Δ | Δ | Δ | Δ |
| 39 | | | | + | | | + | + | | Δ | Δ | Δ | Δ | Δ |
| 40 | | | | + | | | + | | + | Δ | Δ | Δ | Δ | Δ |
| 41 | | | | | + | + | | + | | Δ | Δ | Δ | Δ | Δ |
| 42 | | | | | + | + | | | + | Δ | Δ | Δ | Δ | Δ |
| 43 | | | | | + | | + | + | | Δ | Δ | Δ | Δ | Δ |
| 44 | | | | | + | | + | | + | Δ | Δ | Δ | Δ | Δ |

Explanation of Table 5 and Table 6

Table 5 shows the results of deodorant tests using *Lactobacillus deodorans* instead of *Lactobacillus clearans*, and Table 6 shows the results of deodorant tests using a mixed strain of *Lactobacillus sulfurica* and *Lactobacillus nitrosus*, instead of *Lactobacillus clearans*.

From the results of experiments using *Lactobacillus deodorans*, instead of *Lactobacillus clearans*, almost the same tendency as in Table 4 was noted.

Here, it is to be noted that the deodorant effect shown by the symbol ◎ in the cases where Lactobacillus plus the ⓐ strain were used is different in the degree of deodorizing feces, from that shown by the same symbol ◎ in the cases where *Lactobacillus clearans* plus the ⓐ strain were used. For example, when administration of *Lactobacillus clearans* only was stopped, the offensive odor which had been reduced to half of original revived soon, while when *Lactobacillus clearans* was administered in combination with the ⓐ strain, such revival ceased at a quarter of the original and the influence of the administration remained for three days after the stoppage thereof. In contrast, when *Lactobacillus deodorans* was administered alone, the offensive odor was removed completely for a while. However, when *Lactobacillus deodorans* was administered in combination with the ⓐ strain, the time necessary for reaching complete deodorization was shortened and the effect continued, in many cases, for 6–10 days after stopping the administration.

In connection with the revival of the odor of feces, the state of intestinal bacteria of the test subjects was examined. When *Lactobacillus clearans* or a mixed strain of *Lactobacillus sulfurica* and *Lactobacillus nitrosus* was used, no change in intestinal bacteria was observed. Even when *Lactobacillus clearans* or a mixed strain of *Lactobacillus sulfurica* and *Lactobacillus nitrosus* was used in combination with the ⓐ strain, the intestinal bacteria was restored to the original state within 5 days or so. However, when *Lactobacillus deodorans* was used, 15 days or so were generally required for restoration and the intestinal bacteria sometimes showed a change (reduction) in many cases. In the case, the restoration was not complete in some cases. The difference of effects exerted on the intestinal bacteria by *Lactobacillus clearans* and *Lactobacillus deodorans* is a characteristic thereof.

Table 6 shows that, when a mixed strain of *Lactobacillus sulfurica* and *Lactobacillus nitrosus* was used, almost the same results as the case of using *Lactobacillus clearans* were obtained with respect to rate strength and period of the deodorant effect.

EXAMPLE 6

As shown in Tables 4–6, when two, three or four kinds of strains according to the present invention were administered to man in combination, there were many experimental sections where a definite difference could hardly be recognized under the above-mentioned standard of judgement. Therefore, the degrees of the growth of chickens and pigs were also investigated.

The strains were added to feed stuff in the following amount:

For chickens: Each strain was added in an amount of 0.2 g as dry cells containing extending agents, per 1 kg of usual assorted feed for chickens.

For pigs: Each strain was added in an amount of 0.4 g as dry cells containing extending agents, per 1 kg of usual assorted feed for pigs.

The investigation was effected mainly by comparing the weight and the state of flesh of chickens or pigs after the administration, with those before the administration.

Thus, it was found that, in the experimental sections where *Lactobacillus deodorans, Lactobacillus clearans* or a mixed strain of *Lactobacillus sulfurica* and *Lactobacillus nitrosus* was used in combination with Bifidobacterium (ⓐ strain or ⓑ strain) or in combination with Bacillus (A strain or B strain) and also in the experimental sections where *Lactbacillus deodorans, Lactobacillus clearans* or a mixed strain of *Lactobacillus sulfurica* and *Lactobacillus nitrosus* was used in combination with *Streptococcus faecalis* and Bifidobacterium or Bacillus or in combination with *Streptococcus faecalis,* Bifidobacterium and Bacillus, the feeding efficiency was improved by 10% or so, compared with the cases wherein *Lactobacillus deodorans, Lactobacillus clearans* or a mixed strain of *Lactobacillus sulfurica* and *Lactbacillus nitrosus* was added solely to the feed stuff.

EXAMPLE 7

An absorbent cotton well dipped in a solution of 5 mg of chlorohexidine hydrochloride in 250 ml of water was inserted into the vagina of a patient, in whose vagina Lactobacillus was reduced to one-hundredth or less of the normal value, three-times for 15 minutes each. Then, another cotton well dipped in a culture solution of each of *Lactobacillus clearans, Lactobacillus clearans* plus the ⓐ strain, *Lactobacillus deodorans,* and *Lactobacillus deodorans* plus the ⓐ strain, which were provided with resistance against 5γ chlorohexidine hydrochloride solution, was inserted into the vagina of the above patient, and the absorbent cotton was exchanged for new one, five times at intervals of one hour. The test was carried out with 15 persons for each test section.

At the same time, the prudenda or vulvo of the patient was treated three-times with a disinfectant to control contaminated bacteria, and then absorbent cotton well dipped in the culture solution of each of the above-mentioned strains was applied to the prudenda.

The treatment as above was continued for one week. After 2 days, the presence of many Lactobacillus was observed in the vagina, almost without exception or vulvo. However, after a further 5 days, the survival ratio of Lactobacillus in those test sections were *Lactobacillus clearans* was used in combination with the ⓐ strain was higher than that of the test sections where the ⓐ strain was not used in combination, although reduction of Lactbacillus as noted before the start of the test was observed in some patients treated with *Lactobacillus clearans.*

As regards the ratio of removing offensive odor, a distinct difference was recognized between the test sections where the ⓐ strain was used in combination and the test sections where the ⓐ strain was not used in combination. (The deodorant effect was superior in the former test sections to the latter test sections.)

In case of a sole use of *Lactobacillus deodorans,* deodorizing efficiency and survival count is extraordinary superior to those of *Lactobacillus clearans.* Further addition of the ⓐ strain shows more solid results.

TABLE 7

| Strain used (Strain resistant to drugs is used) | Results of observation on the seventh day | | | |
|---|---|---|---|---|
| | *Lactobacillus clearans* | *Lactobacillus clearans* plus ⓐ strain | *Lactobacillus deodorans* | *Lactobacillus deodorans* plus ⓐ strain |
| No. of Test Subjects | 15 persons | 15 persons | 15 persons | 15 persons |
| Effective Instances | 4 persons | 5 persons | 7 persons | 11 persons |
| Ineffective Instances | 8 persons | 7 persons | 4 persons | 2 persons |
| Slightly effective* Instances | 3 persons | 3 persons | 4 persons | 2 persons |

*Slight effect appeared and then reduced gradually.

The same results were obtained when using *Lactobacillus clearans, Lactobacillus deodorans,* a mixture of *Lactobacillus nitrosus* and *Lactobacillus sulfurica,* and *Streptocuccus faecalis* other than the IFO Nos. 14253, 14450, 14257, 14255, 14452 and 14453.

While the invention has been described in detail and with reference to specific embodiments thereof, it will be apparent to one skilled in the art that various changes and modification can be made therein without departing from the spirit and scope of thereof.

What is claimed is:

1. A process for deodorizing in vivo comprising administering a biodeodorizer comprising (a) at least one strain selected from the group consisting of *Lactobacillus deodorans, Lactobacillus clearans* and a mixed strain of *Lactobacillus sulfurica* and *Lactobacillus nitrosus* and (b) *Streptococcus faecalis* having the ability to produce antibiotics, wherein the proportion of Lactobacillus to *Streptococcus faecalis* is about 150:1 to about 0.01:1.

* * * * *